United States Patent
Elsmark et al.

(10) Patent No.: US 12,321,486 B2
(45) Date of Patent: Jun. 3, 2025

(54) PROVIDING DATA FOR TRAINING A MACHINE LEARNING MODEL

(71) Applicant: ASSA ABLOY AB, Stockholm (SE)

(72) Inventors: Lars Elsmark, Saltsjö-Boo (SE); Kenneth Pernyer, Stockholm (SE)

(73) Assignee: ASSA ABLOY AB, Stockholm (SE)

( * ) Notice: Subject to any disclaimer, the term of this patent is extended or adjusted under 35 U.S.C. 154(b) by 253 days.

(21) Appl. No.: 18/029,825

(22) PCT Filed: Oct. 1, 2021

(86) PCT No.: PCT/EP2021/077080
§ 371 (c)(1),
(2) Date: Mar. 31, 2023

(87) PCT Pub. No.: WO2022/069700
PCT Pub. Date: Apr. 7, 2022

(65) Prior Publication Data
US 2023/0367900 A1    Nov. 16, 2023

(30) Foreign Application Priority Data
Oct. 2, 2020   (SE) .................................... 2051156-4

(51) Int. Cl.
G06F 21/62    (2013.01)
G06F 21/60    (2013.01)
H04L 9/08     (2006.01)

(52) U.S. Cl.
CPC ........ *G06F 21/6245* (2013.01); *G06F 21/606* (2013.01); *H04L 9/0819* (2013.01); *G06F 2221/2115* (2013.01)

(58) Field of Classification Search
CPC .................................................. G06F 21/6245
See application file for complete search history.

(56) References Cited

U.S. PATENT DOCUMENTS 10,685,748 B1    6/2020  Chappell et al.
2016/0078361 A1  3/2016  Brueckner et al.
(Continued)

FOREIGN PATENT DOCUMENTS

CN          111260053        6/2020
WO     WO 2020/127475        6/2020

OTHER PUBLICATIONS

Official Action for Sweden Patent Application No. 2051156-4, dated Jun. 7, 2021, 11 pages.
(Continued)

*Primary Examiner* — Simon P Kanaan
(74) *Attorney, Agent, or Firm* — Schwegman Lundberg & Woessner, P.A.

(57) ABSTRACT

It is provided a method for providing data for training a machine learning model. The method is performed in a training data provider (1) and comprises the steps of: obtaining (40) a data structure comprising a chain of delegations, the chain of delegations covering a delegation path from a media capturing device (3) to the training data provider (1) such that, in the chain of delegations, each delegation is a delegation from a delegator to a receiver; sending (42) a key request to a delegation verifier (2), the key request comprising the data structure; receiving (44) a decryption key from the delegation verifier (2); obtaining (46) encrypted media data captured by the media capturing device (3); decrypting (48) the encrypted media data, resulting in decrypted media data; and providing (50) the decrypted media data for training the machine learning model.

20 Claims, 3 Drawing Sheets

(56) References Cited

U.S. PATENT DOCUMENTS

| | | |
|---|---|---|
| 2018/0255023 A1 | 9/2018 | Whaley et al. |
| 2018/0306609 A1 | 10/2018 | Agarwal et al. |
| 2019/0370634 A1 | 12/2019 | Ferreira Moreno et al. |
| 2020/0017117 A1 | 1/2020 | Milton |
| 2020/0151516 A1 | 5/2020 | Anushiravani et al. |
| 2021/0263779 A1* | 8/2021 | Haghighat ............ G06F 9/5061 |
| 2022/0075793 A1* | 3/2022 | Jezewski .................. G06N 5/04 |
| 2023/0367900 A1* | 11/2023 | Elsmark .............. G06F 21/6245 |

OTHER PUBLICATIONS

International Search Report and Written Opinion for International (PCT) Patent Application No. PCT/EP2021/077080, dated Jan. 19, 2022, 13 pages.

* cited by examiner

PROVIDING DATA FOR TRAINING A MACHINE LEARNING MODEL

CROSS REFERENCE TO RELATED APPLICATIONS

This application is a national stage application under 35 U.S.C. 371 and claims the benefit of PCT Application No. PCT/EP2021/077080 having an international filing date of Oct. 1, 2021, which designated the United States, which PCT application claimed the benefit of Sweden Patent Application No. 2051156-4 filed Oct. 2, 2020, the disclosure of each of which are incorporated herein by reference.

TECHNICAL FIELD

The present disclosure relates to the field of machine learning and in particular to providing data for training a machine learning model.

BACKGROUND

New technology opens up new opportunities. For instance, the evolution of digital cameras and communication technologies enable monitoring of people to be provided using video surveillance at relatively low cost. This can be particularly useful for elderly people or disabled people, who in this way can enjoy greatly improved quality of life by living in their own home instead of being in a staffed care facility.

Video surveillance is certainly useful, but privacy issues arise. Hardly anyone enjoys being continuously monitored using video surveillance, even if it is mainly used for machine-based monitoring of when the person needs help. When machine-based monitoring relies on a machine learning model, this model needs to be trained. Training of the machine learning model can be performed prior to deployment and can also occur over time, after deployment. Such continued training enables the machine learning model to improve and adapt over time, which improves the performance of the machine learning model.

However, also the training is based on video and/or audio data from people being monitored, which can be a privacy concern.

SUMMARY

One object is to provide a solution where a person being monitored can control when data from the monitoring can be used for training a machine learning model.

According to a first aspect, it is provided a method for providing data for training a machine learning model. The method is performed in a training data provider and comprises the steps of: obtaining a data structure comprising a chain of delegations, the chain of delegations covering a delegation path from a media capturing device via at least one intermediate party to the training data provider such that, in the chain of delegations, each delegation is a delegation from a delegator to a receiver; sending a key request to a delegation verifier, the key request comprising the data structure; receiving a decryption key from the delegation verifier; obtaining encrypted media data captured by the media capturing device; decrypting the encrypted media data, resulting in decrypted media data; and providing the decrypted media data for training the machine learning model.

The data structure may further comprise at least one condition of providing a decryption key.

The at least one condition may comprise a time window that needs to be satisfied.

The at least one condition may comprise a type of event that needs to be detected in the media data.

The at least one condition may be a combination of conditions to be evaluated using logical AND and/or logical OR operations.

In the chain of delegations, a delegation from the media capturing device may be digitally signed.

Training of the machine learning model based on data from the media capturing device may be prevented when at least one delegation in the chain of delegations comprises a constraint indicating that training is not allowed.

The step of receiving is conditional on the delegation verifier verifying chain of delegations.

The data structure may comprise the decryption key, encrypted to be decryptable by the delegation verifier.

The decrypted media data may comprise video data and/or audio data.

According to a second aspect, it is provided a training data provider for providing data for training a machine learning model. The training data provider comprises: a processor; and a memory storing instructions that, when executed by the processor, cause the training data provider to: obtain a data structure comprising a chain of delegations, the chain of delegations covering a delegation path from a media capturing device via at least one intermediate party to the training data provider such that, in the chain of delegations, each delegation is a delegation from a delegator to a receiver; send a key request to a delegation verifier, the key request comprising the data structure; receive a decryption key from the delegation verifier; obtain encrypted media data captured by the media capturing device; decrypt the encrypted media data, resulting in decrypted media data; and provide the decrypted media data for training the machine learning model.

The data structure may further comprise at least one condition of providing a decryption key.

The at least one condition may comprise a time window that needs to be satisfied.

The at least one condition may comprise a type of event that needs to be detected in the media data.

The at least one condition may be a combination of conditions to be evaluated using logical AND and/or logical OR operations.

In the chain of delegations, a delegation from the media capturing device may be digitally signed.

Training of the machine learning model based on data from the media capturing device may be prevented when at least one delegation in the chain of delegations comprises a constraint indicating that training is not allowed.

The instructions to receive may be conditional on the delegation verifier verifying chain of delegations.

The data structure may comprise the decryption key, encrypted to be decryptable by the delegation verifier.

The decrypted media data may comprise video data and/or audio data.

According to a third aspect, it is provided a computer program for providing data for training a machine learning model. The computer program comprises computer program code which, when executed on a training data provider causes the training data provider to: obtain a data structure comprising a chain of delegations, the chain of delegations covering a delegation path from a media capturing device via at least one intermediate party to the training data provider such that, in the chain of delegations, each delegation is a delegation from a delegator to a receiver; send a key request to a delegation verifier, the key request comprising the data structure; receive a decryption key from the delegation verifier; obtain encrypted media data captured by the media capturing device; decrypt the encrypted media data, resulting in decrypted media data; and provide the decrypted media data for training the machine learning model.

According to a fourth aspect, it is provided a computer program product comprising a computer program according to the third aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

Aspects and embodiments are now described, by way of example, with reference to the accompanying drawings, in which.

DETAILED DESCRIPTION

The aspects of the present disclosure will now be described more fully hereinafter with reference to the accompanying drawings, in which certain embodiments of the invention are shown. These aspects may, however, be embodied in many different forms and should not be construed as limiting; rather, these embodiments are provided by way of example so that this disclosure will be thorough and complete, and to fully convey the scope of all aspects of invention to those skilled in the art. Like numbers refer to like elements throughout the description.

Embodiments presented herein provide improved training of a machine learning model based on sensitive data (e.g. video/audio) of a monitored person. Specifically, a training data provider is provided a delegation of a right to consume the sensitive data, wherein the delegation passes from the media capturing device, via at least one intermediate party, to the training data provider. Using the intermediate party, the monitored person does not need to know the exact party that should be allowed to train the machine learning model, as long as the monitored person trusts the intermediate party.

Figure 1:
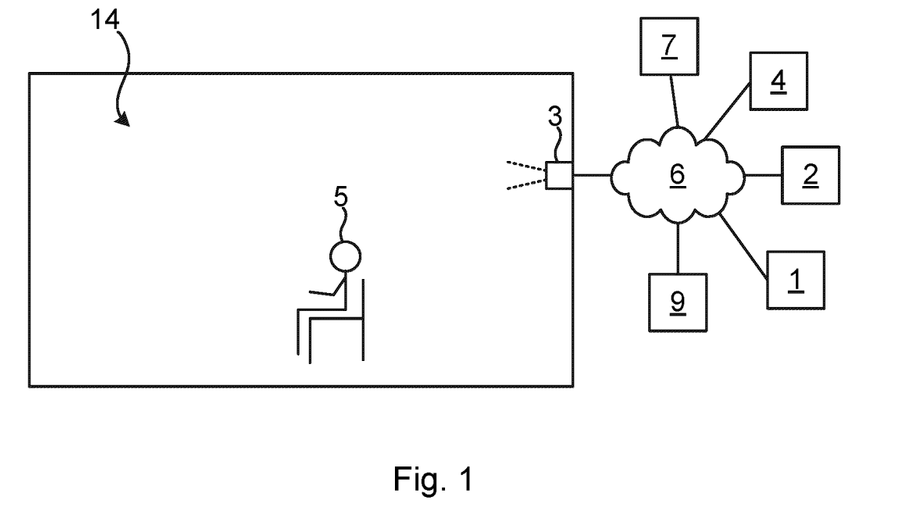
FIG. 1 is a schematic diagram illustrating an environment in which embodiments presented herein can be applied.

FIG. 1 is a schematic diagram illustrating an environment in which embodiments presented herein can be applied. A person 5 to be monitored is at least part of the time present in a physical space 14. The physical space 14 can e.g. be a room, a flat, a house, an office etc.

A media capturing device 3 is provided to monitor the person 5 (hereinafter referred to as the monitored person) in the physical space 14. There can be multiple media capturing devices 3 for difference media types and/or to cover a larger area. Each media capturing device 3 captures media data containing any one or more of video, audio, radar, infrared sensor, etc.

Each media capturing device 3 is connected to a network 6, which can be an internet protocol (IP) based network. The network can e.g. comprise any one or more of a local wireless network, a cellular network, a wired local area network, a wide area network (such as the Internet), etc.

A machine learning model device 9 is also connected to the network 6. The machine learning model device 9 infers one or more results based on input data, in the form of media data from the media capturing device(s) 3. Non-limiting examples of results being types of events that can be inferred by the machine learning model include: lying on the floor, breathing, screaming, a specific gesture, absent person, present person, etc. The results can be used to determine whether to trigger an alarm to help the monitored person 5. The alarm can e.g. result in assigning caregivers or medical personnel to go to the physical space 14 when the monitored person 5 is in need of help. As explained in more detail below, the machine learning model is trained based on media data from the media capturing device(s) 3, controlled by a training data provider 1.

The media data from the media capturing device 3 is encrypted, e.g. with a symmetric key allowing efficient encryption and decryption. The decryption key to decrypt the encrypted media data is then the same as the encryption key. Optionally, the encryption key is different in accordance with one or more rules. For instance, the encryption key can vary based over time or, e.g. to allow one group of receivers to decrypt the media data only during daytime hours and another group of receivers to decrypt the media data during night-time hours.

Optionally, the data from the media capturing device is first transferred, in encrypted form, from the media capturing device 3 to a media server 4. In such a case, the training data provider 1 first obtains a decryption key from a delegation verifier 2, and uses the decryption key to decrypt encrypted media data obtained from the media server 4.

The media server 4 is any suitable server which is able to receive media data in encrypted form from the media capturing device 3, store the media data and supply the media data to the training data provider 1.

The delegation verifier 2 is any suitable server which is able to verify a delegation chain provide supply a decryption key to a training data provider when a valid key request comprising the delegation chain is received from the training data provider. Optionally, the media server 4 and the delegation verifier can be combined in a single server.

One or more intermediate parties 7 are provided to simplify the delegation of the right to use sensitive data for training the machine learning model 9, as explained in more detail below.

Figure 2A:
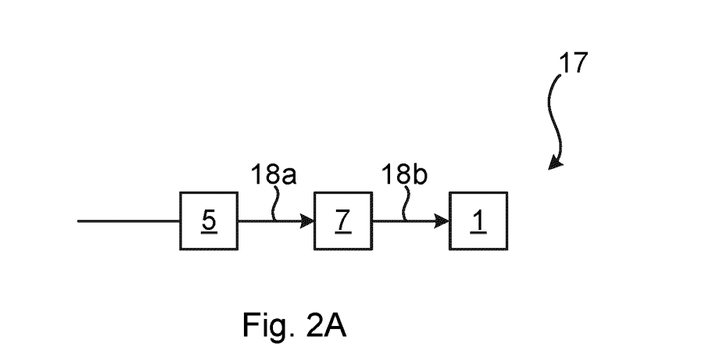
FIGS. 2A-B are schematic diagrams illustrating the concept of a delegation chain which can be applied in the environment of FIG. 1.
Figure 2B:
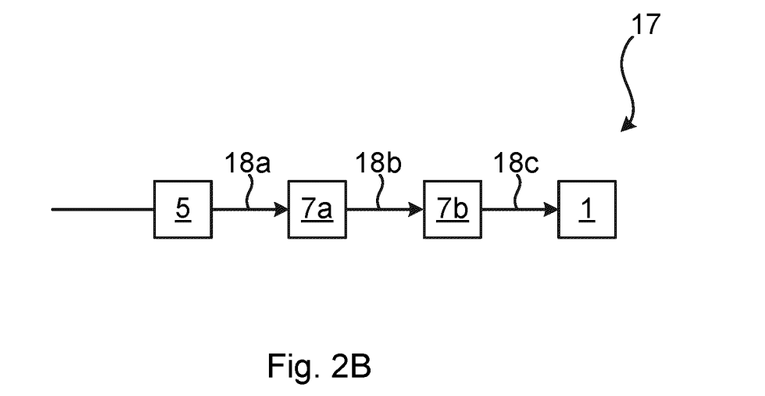

FIGS. 2A-B are schematic diagrams illustrating the concept of a delegation chain 17 which can be applied in the environment of FIG. 1.

Looking first to FIG. 2A, a delegation chain 17 is here made up of two delegations: a first delegation 18a from the monitored person 5 to an intermediate party 7 and a second delegation 18b from the intermediate party 7 to the training data provider 1. The intermediate party 7 can e.g. be a family member of the monitored person 5, a care giver or a municipality.

In the example illustrated in FIG. 2B, there are multiple intermediate parties 7a, 7b in the delegation chain 17. In this example, the delegation chain 17 comprises a first delegation 18a from the monitored person 5 to first intermediate party 7a, a second delegation 18b from the first intermediate party 7a to a second intermediate party 7b and a third delegation 18c from the second intermediate party 7b to the training data provider 1.

In one example, the first intermediate party 7a is a municipality or other public body that the monitored person 5 trusts and the second intermediate party 7b is a caregiver. In another example, the first intermediate party 7a is a family member of the monitored person 5 and the second intermediate party 7b is a caregiver.

It is to be noted that the delegation chain 17 can contain any number of delegations as long as the delegation chain comprises an unbroken delegation chain from the monitored person 5 to the training data provider 1.

Figure 3:
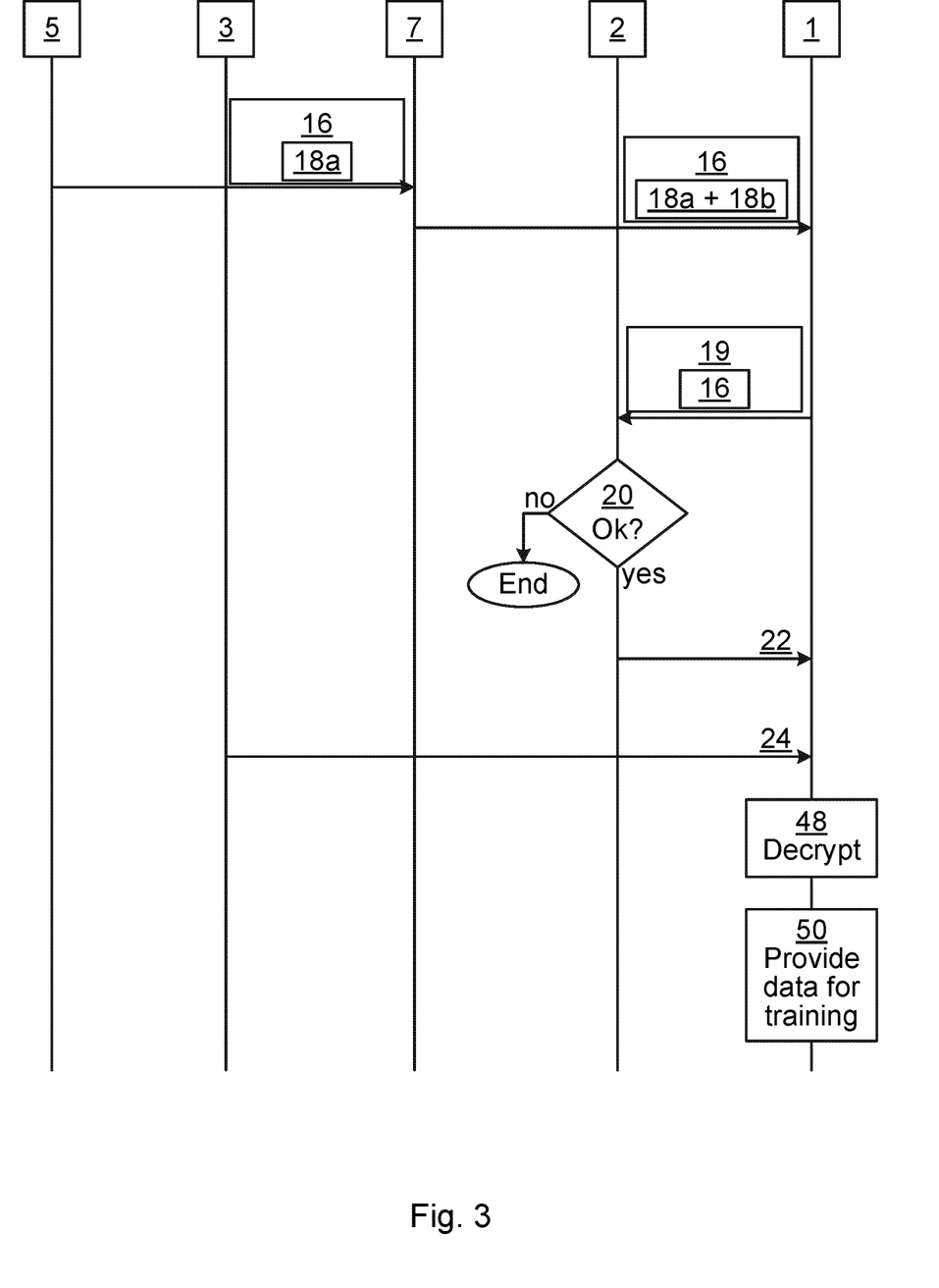
FIG. 3 is a sequence diagram illustrating how data for training a machine learning model can be provided in a secure and reliable way.

FIG. 3 is a sequence diagram illustrating how data for training a machine learning model can be provided in a secure and reliable way.

The monitored person 5 (or a person authorised to act in her place) starts a delegation chain by creating a first delegation 18a to delegate access to media data for training a machine learning model. The first delegation 18a is included in a data structure 16 which is transmitted to an intermediate party 7, such as a care giver or a municipality. Optionally, the data structure 16 also includes one or more conditions for providing the decryption key. The one or more conditions can be included in each delegation or could be provided separately from the delegation(s). The delegation can be cryptographically signed to prove validity, which, when one or more conditions are included in the delegation, also proves validity of the condition(s).

In one embodiment, the decryption key for decrypting the media data can be included in the data structure 16, but the decryption key is itself encrypted. The decryption key can be encrypted with an asymmetric key for the delegation verifier 2. In other words, it is then only the delegation verifier 2 that can decrypt the encrypted decryption key.

For instance, one condition can be a time window restricting access to media data only during a specified time. Such a time window can be synchronised with different encryption keys being used to encrypt the media data at different hours, as described above. For instance, during daytime, the media data is allowed to be decrypted to be used for training a machine learning model, while this might not be allowed at night-time, when only authorised care personnel can access and decrypt the media data. Alternatively or additionally, one condition can be that a specified type of event occurs in the media data. Such event can e.g. be that a person falls, that a person leaves her bed at night, the person signals an alarm signal and/or that a person exits the front door without a coat. Another type of condition can be that an alarm has been triggered. The events can be particularly applicable when the value of the base set of training data declines over time from a training perspective. At that stage, the use of events provides significantly more relevant training data.

The intermediate party 7 generates a new delegation 18b to the training data provider 1 and both delegations 18a, 18b are included in the data structure 16 provided to the training data provider 1. Together, the delegations 18a, 18b make up a chain of delegations. Optionally, the intermediate party 7 can restrict the condition(s), when present, in the data structure 16 further, but not broaden the condition(s). For instance, the intermediate party can restrict a time window even further and/or remove a type of event that is allowable.

In order to request a decryption key for media data, the training data provider 1 sends a key request 19, containing the data structure 16 comprising the chain of delegations 18a, 18b, and optionally one or more conditions, to the delegation verifier 2.

Each delegation 18a, 18b is a delegation from a delegator to a receiver of a right to perform an action. In other words, each delegation is a data item containing a data field for the delegator and a data field for the receiver. In this case, the delegation implies the right to use data captured by the media capturing device for training a machine learning model.

The delegation verifier 2 verifies the chain of delegations of the key request. The verification comprises verifying that the delegation chain comprises an unbroken delegation chain from the media capturing device 3 to the training data provider. Moreover, the verification may include verification of cryptographic signatures of one or more of the delegations of the delegation chain. When the data structure comprises one or more conditions associated with the delegation chain, these conditions are enforced by the delegation verifier 2, optionally by using an external entity. All time restrictions in the delegation chain must pass the verification for the whole delegation chain to pass the verification.

When a condition includes that a type of event needs to be detected in the media data, this event detection can be based on a machine-learning model. The event detection can be performed by the delegation verifier 2 itself or by an external entity, e.g. making use of another machine-learning model than the one being trained by this method. Manually triggered events are also possible, e.g. alarm signal from the person being monitored or an event classification by an operator viewing the data. Manually triggered events can also be applied retroactively. For instance, if a home care worker arrives at the home of a monitored person and discovers that the monitored person has fallen down, this is an evident event that the person has fallen down. However, the time when that happened is in the past (from the discovery). The event is thus associated with a time range, e.g. in the past x hours prior to the discovery (e.g. based on when it is known that the monitored person was moving about, determined autonomously or manually). Hence, the event detection can be based on autonomously triggered events or manually triggered events. When the data structure comprises an encrypted form of the decryption key, the delegation verifier decrypts the encrypted decryption key to obtain a decryption key 22 that can be provided to the training data provider 1, when verification is positive.

If the verification fails, the method ends. Otherwise, when the verification passes, the delegation verifier sends a decryption key 22 to the training data provider 1.

The training data provider 1 receives encrypted media data 24 from the media capturing device 3 and decrypts 48 the data using the decryption key 22.

The decrypted media data is then provided 50 for training the machine learning model.

Figure 4:
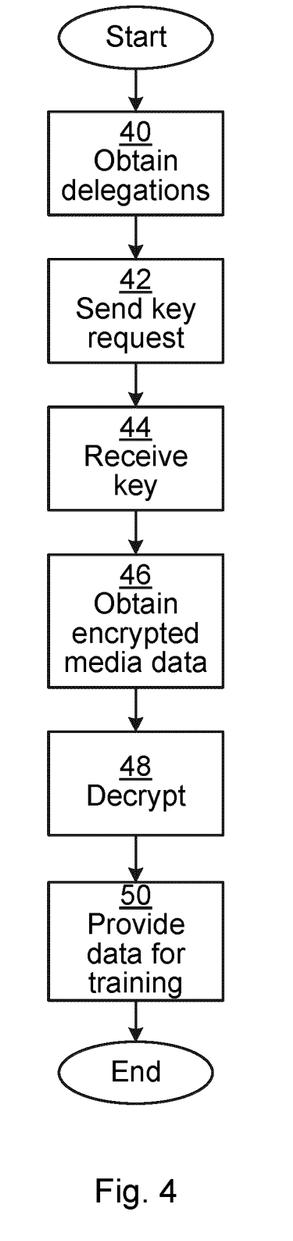
FIG. 4 is a flow chart illustrating embodiments of a method for providing data for training a machine learning model.

FIG. 4 is a flow chart illustrating embodiments of a method for providing data for training a machine learning model. The method is performed in the training data provider 1. The method corresponds to the actions of the training data provider 1 in the sequence diagram of FIG. 3, described above.

In an obtain delegations step 40, the training data provider 1 obtains a data structure comprising chain of delegations. The chain of delegations covers a delegation path from a monitored person 5 (the media capturing device 3), via at least one intermediate party, 7, 7a, 7b to the training data provider 1. In the chain of delegations, each delegation is a delegation from a delegator to a receiver. In any intermediate nodes in the chain, the node is a receiver of a one delegation and a delegator of the subsequent delegation, thus creating the delegation chain. In the chain of delegations, a delegation from the monitored person 5 can be digitally signed. In one embodiment, each delegation in the chain of delegation is digitally signed by the delegator of the respective delegation. When one or more conditions are included in the data structure, each digital signature is an indication of approval of the use of the associated media data as long as the one or more conditions are satisfied. The data structure can be received by the party being the delegator of the last delegation in the delegation chain, i.e. the last intermediate party.

Optionally, the data structure further comprises at least one condition of providing a decryption key. Such at least one condition can e.g. comprise a time window that needs to be satisfied. Alternatively or additionally, the at least one condition comprises a type of event that needs to be detected. When present, the at least one condition is checked by the delegation verifier or its checking is coordinated by the delegation verifier. The event can have a time range associated with it. The time range can include time in the past and/or time in the future. The time range can also be open-ended either in the beginning or the end.

Optionally, the at least one condition is a combination of conditions to be evaluated using logical AND and/or logical OR operations. This allows a flexible evaluation of the set of conditions. For instance, the combination can be evaluated if the following is true: "(the time is between 9 a.m. and 5 p.m., Monday to Friday) OR (an emergency event is detected)".

In one embodiment, at least one delegation in the chain of delegations comprises a time constraint. This allows the monitored person 5 to limit media data from the media capturing device 3 to only be used as training data e.g. during hours when the monitored person 5 is usually awake.

Optionally, the data structure further comprises at structure comprises the decryption key, encrypted to be decryptable by the delegation verifier 2. For instance, the decryption key can be encrypted with an asymmetric encryption.

In a send key request step 42, the training data provider 1 sends a key request to a delegation verifier 2. The key request comprises the data structure that comprises the chain of delegations and optionally one or more conditions to be verified by the delegation verifier. The key request indicates to the delegation verifier that the training data provider requests a decryption key to be used for decrypting media data for training a machine learning model.

In a receive key step 44, the training data provider receives a decryption key from the delegation verifier 2. As explained above with reference to FIG. 3, prior to the key being received, the delegation verifier 2 has verified the chain of delegations and any conditions that may be provided in the data structure. Optionally, the training data provider 1 checks the delegation chain prior to sending the key request to prevent unnecessary processing when the delegation chain is not valid. In any case, the delegation verifier 2 only provides the decryption key when the delegation chain is valid, allowing using the data from the media capturing device as training data for the machine learning model.

In this way, training of the machine learning model based on data from the media capturing device 3 can be prevented when at least one delegation in the chain of delegations comprises a constraint indicating that training is not allowed.

The decryption key can be a symmetric key, which allows for more resource efficient encryption and decryption. Alternatively, the decryption key is an asymmetric key.

In an obtain encrypted media data step 46, the training data provider 1 obtains encrypted media data captured by the media capturing device 3. The encrypted media data can be obtained as one or more files and/or a media stream from the media capturing device 3, optionally via a media server 4 (see FIG. 1).

In a decrypt step 48, the training data provider 1 decrypts the encrypted media data, resulting in decrypted media data. The decrypted media data can comprise video data and/or audio data.

In a provide data for training step 50, the training data provider 1 provides the decrypted media data for training the machine learning model 9. The training can be performed by the training data provider 1 and/or the machine learning model 9 itself.

Using the embodiments presented herein, the monitored user is provided with peace of mind that she/he can control what party is allowed to train machine learning models based on the data capturing by the media capturing device. This greatly improves trust and control over privacy. At the same time, the training data provider can use the training data when allowed to improve the performance of the machine learning model.

Figure 5:
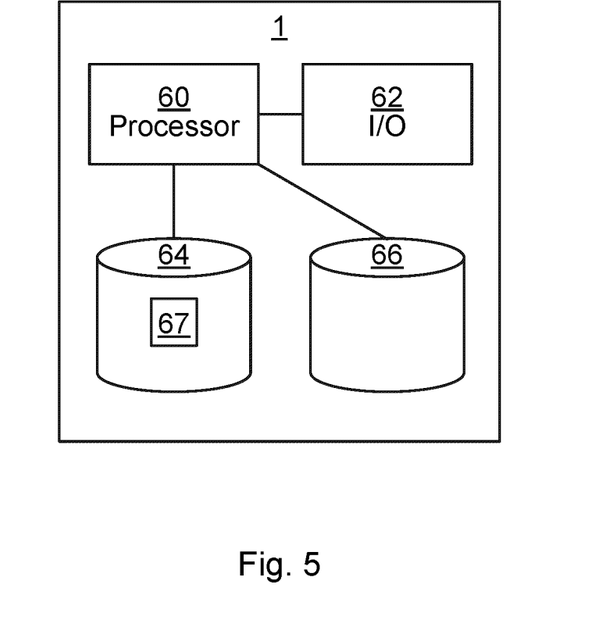
FIG. 5 is a schematic diagram illustrating components of the training data provider of FIG. 1.

FIG. 5 is a schematic diagram illustrating components of the training data provider 1 of FIG. 1. A processor 60 is provided using any combination of one or more of a suitable central processing unit (CPU), graphics processing unit (GPU), multiprocessor, microcontroller, digital signal processor (DSP), etc., capable of executing software instructions 67 stored in a memory 64, which can thus be a computer program product. The processor 60 could alternatively be implemented using an application specific integrated circuit (ASIC), field programmable gate array (FPGA), etc. The processor 60 can be configured to execute the method described with reference to FIG. 4 above.

The memory 64 can be any combination of random-access memory (RAM) and/or read-only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of RAM and/or ROM.

The training data provider 1 further comprises an I/O interface 62 for communicating with external and/or internal entities. Optionally, the I/O interface 62 also includes a user interface.

Other components of the training data provider 1 are omitted in order not to obscure the concepts presented herein.

Figure 6:
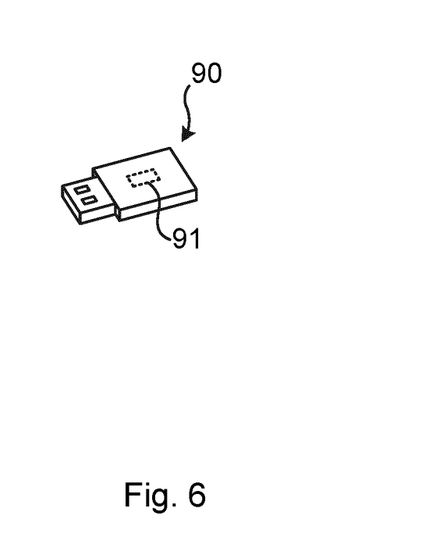
FIG. 6 shows one example of a computer program product comprising computer readable means.

FIG. 5 shows one example of a computer program product 90 comprising non-transitory computer readable means. On this computer readable means, a computer program 91 can be stored, which computer program can cause a processor to execute a method according to embodiments described herein. In this example, the computer program product is in the form of a removable solid-state memory, e.g. a Universal Serial Bus (USB) drive. As explained above, the computer program product could also be embodied in a memory of a device, such as the computer program product 64 of FIG. 4. While the computer program 91 is here schematically shown as a section of the removable solid-state memory, the computer program can be stored in any way which is suitable for the computer program product, such as another type of removable solid-state memory, or an optical disc, such as a CD (compact disc), a DVD (digital versatile disc) or a Blu-Ray disc.

Here now follows a list of enumerated embodiments.

i. A method for providing data for training a machine learning model, the method being performed in a training data provider and comprising the steps of:
obtaining a data structure comprising a chain of delegations, the chain of delegations covering a delegation path from a media capturing device to the training data provider such that, in the chain of delegations, each delegation is a delegation from a delegator to a receiver;
sending a key request to a delegation verifier, the key request comprising the data structure;
receiving a decryption key from the delegation verifier;
obtaining encrypted media data captured by the media capturing device;
decrypting the encrypted media data, resulting in decrypted media data; and
providing the decrypted media data for training the machine learning model.

ii. The method according to embodiment i, wherein the data structure further comprises at least one condition of providing a decryption key.

iii. The method according to embodiment ii, wherein the at least one condition comprises a time window that needs to be satisfied.

iv. The method according to embodiment ii or iii, wherein the at least one condition comprises a type of event that needs to be detected in the media data.

v. The method according to any one of the preceding embodiments, wherein, in the chain of delegations, a delegation from the media capturing device is digitally signed.

vi. The method according to any one of the preceding embodiments, wherein training of the machine learning model based on data from the media capturing device is prevented when at least one delegation in the chain of delegations comprises a constraint indicating that training is not allowed.

vii. The method according to any one of the preceding embodiments, wherein the step of receiving is conditional on the delegation verifier verifying chain of delegations.

viii. The method according to any one of the preceding embodiments, wherein the data structure comprises the decryption key, encrypted to be decryptable by the delegation verifier.

ix. The method according to any one of the preceding embodiments, wherein the decrypted media data comprises video data.

x. The method according to any one of the preceding embodiments, wherein the decrypted media data comprises audio data.

xi. A training data provider for providing data for training a machine learning model, the training data provider comprising:
a processor; and
a memory storing instructions that, when executed by the processor, cause the training data provider to:
obtain a data structure comprising a chain of delegations, the chain of delegations covering a delegation path from a media capturing device to the training data provider such that, in the chain of delegations, each delegation is a delegation from a delegator to a receiver;
send a key request to a delegation verifier, the key request comprising the data structure;
receive a decryption key from the delegation verifier;
obtain encrypted media data captured by the media capturing device;
decrypt the encrypted media data, resulting in decrypted media data; and
provide the decrypted media data for training the machine learning model.

xii. The training data provider according to embodiment xi, wherein the data structure further comprises at least one condition of providing a decryption key.

xiii. The training data provider according to embodiment xii, wherein the at least one condition comprises a time window that needs to be satisfied.

xiv. The training data provider according to embodiment xii or xiii, wherein the at least one condition comprises a type of event that needs to be detected in the media data.

xv. The training data provider according to any one of embodiments xi to xiv, wherein, in the chain of delegations, a delegation from the media capturing device is digitally signed.

xvi. The training data provider according to any one of embodiments xi to xv, wherein training of the machine learning model based on data from the media capturing device is prevented when at least one delegation in the chain of delegations comprises a constraint indicating that training is not allowed.

xvii. The training data provider according to any one of embodiments xi to xvi, wherein the instructions to receive are conditional on the delegation verifier verifying chain of delegations.

xviii. The training data provider according to any one of embodiments xi to xvii, wherein the data structure comprises the decryption key, encrypted to be decryptable by the delegation verifier.

xix. The training data provider according to any one of embodiments xi to xviii, wherein the decrypted media data comprises video data.

xx. The method according to any one of the preceding embodiments xi to xix, wherein the decrypted media data comprises audio data.

xxi. A computer program for providing data for training a machine learning model, the computer program comprising computer program code which, when executed on a training data provider causes the training data provider to:
obtain a data structure comprising a chain of delegations, the chain of delegations covering a delegation path from a media capturing device to the training data provider such that, in the chain of delegations, each delegation is a delegation from a delegator to a receiver;
send a key request to a delegation verifier, the key request comprising the data structure;
receive a decryption key from the delegation verifier;
obtain encrypted media data captured by the media capturing device;
decrypt the encrypted media data, resulting in decrypted media data; and
provide the decrypted media data for training the machine learning model.

xxii. A computer program product comprising a computer program according to embodiment xxi and a computer readable means on which the computer program is stored.

The aspects of the present disclosure have mainly been described above with reference to a few embodiments. However, as is readily appreciated by a person skilled in the art, other embodiments than the ones disclosed above are equally possible within the scope of the invention, as defined by the appended patent claims. Thus, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for providing data for training a machine learning model, the method being performed in a training data provider and comprising:
    obtaining a data structure comprising a chain of delegations, the chain of delegations covering a delegation path from a media capturing device via at least one intermediate party to the training data provider such that, in the chain of delegations, each delegation is a delegation from a delegator to a receiver;
    sending a key request to a delegation verifier, the key request comprising the data structure;
    receiving a decryption key from the delegation verifier;
    obtaining encrypted media data captured by the media capturing device;
    decrypting the encrypted media data, resulting in decrypted media data; and
    providing the decrypted media data for training the machine learning model.

2. The method according to claim 1, wherein the data structure further comprises at least one condition of providing a decryption key.

3. The method according to claim 2, wherein the at least one condition comprises a time window that needs to be satisfied.

4. The method according to claim 2, wherein the at least one condition comprises a type of event that needs to be detected in the media data.

5. The method according to claim 2, wherein the at least one condition is a combination of conditions to be evaluated using logical AND and/or logical OR operations.

6. The method according to claim 1, wherein, in the chain of delegations, a delegation from the media capturing device is digitally signed.

7. The method according to claim 1, wherein training of the machine learning model based on data from the media capturing device is prevented when at least one delegation in the chain of delegations comprises a constraint indicating that training is not allowed.

8. The method according to claim 1, wherein receiving is conditional on the delegation verifier verifying chain of delegations.

9. The method according to claim 1, wherein the data structure comprises the decryption key, encrypted to be decryptable by the delegation verifier.

10. The method according to claim 1, wherein the decrypted media data comprises at least one of video data and audio data.

11. A training data provider for providing data for training a machine learning model, the training data provider comprising:
    a processor; and
    a memory storing instructions that, when executed by the processor, cause the training data provider to:
        obtain a data structure comprising a chain of delegations, the chain of delegations covering a delegation path from a media capturing device via at least one intermediate party to the training data provider such that, in the chain of delegations, each delegation is a delegation from a delegator to a receiver;
        send a key request to a delegation verifier, the key request comprising the data structure;
        receive a decryption key from the delegation verifier;
        obtain encrypted media data captured by the media capturing device;
        decrypt the encrypted media data, resulting in decrypted media data; and
        provide the decrypted media data for training the machine learning model.

12. The training data provider according to claim 11, wherein the data structure further comprises at least one condition of providing a decryption key.

13. The training data provider according to claim 12, wherein the at least one condition comprises a time window that needs to be satisfied.

14. The training data provider according to claim 12, wherein the at least one condition comprises a type of event that needs to be detected in the media data.

15. The training data provider according to claim 12, wherein the at least one condition is a combination of conditions to be evaluated using logical AND and/or logical OR operations.

16. The training data provider according to claim 11, wherein, in the chain of delegations, a delegation from the media capturing device is digitally signed.

17. The training data provider according to claim 11, wherein training of the machine learning model based on data from the media capturing device is prevented when at least one delegation in the chain of delegations comprises a constraint indicating that training is not allowed.

18. The training data provider according to claim 11, wherein the instructions to receive are conditional on the delegation verifier verifying chain of delegations.

19. The training data provider according to claim 11, wherein the data structure comprises the decryption key, encrypted to be decryptable by the delegation verifier.

20. A non-transitory computer-readable medium comprising a computer program stored thereon for providing data for training a machine learning model, the computer program comprising computer program code which, when executed on a training data provider causes the training data provider to:
    obtain a data structure comprising a chain of delegations, the chain of delegations covering a delegation path from a media capturing device via at least one intermediate party to the training data provider such that, in the chain of delegations, each delegation is a delegation from a delegator to a receiver;
    send a key request to a delegation verifier, the key request comprising the data structure;
    receive a decryption key from the delegation verifier;
    obtain encrypted media data captured by the media capturing device;
    decrypt the encrypted media data, resulting in decrypted media data; and
    provide the decrypted media data for training the machine learning model.

* * * * *